United States Patent [19]
Eaton

[11] Patent Number: 6,096,079
[45] Date of Patent: Aug. 1, 2000

[54] BONE ANCHORED FIXATION FOR DISPLACEMENT OF FACIAL BONES

[75] Inventor: L. Daniel Eaton, Little Rock, Ark.

[73] Assignee: Board of Trustees of the University of Arkansas, Little Rock, Ark.

[21] Appl. No.: 09/227,270

[22] Filed: Jan. 8, 1999

[51] Int. Cl.⁷ .............................. A61F 2/28; A61F 2/44; A61B 17/56

[52] U.S. Cl. .............................. 623/16; 623/17; 606/53; 606/54; 606/60

[58] Field of Search ..................... 623/16, 17; 606/53, 606/54, 60; 128/898

[56] References Cited

U.S. PATENT DOCUMENTS

| | | |
|---|---|---|
| D. 294,295 | 2/1988 | Branemark . |
| 3,877,424 | 4/1975 | Murray ........................ 128/92 |
| 4,713,003 | 12/1987 | Symington et al. . |
| 4,848,327 | 7/1989 | Perdue ........................ 128/92 |
| 4,976,739 | 12/1990 | Duthie, Jr. . |
| 5,064,374 | 11/1991 | Lundgren . |
| 5,344,457 | 9/1994 | Pilliar et al. . |
| 5,372,598 | 12/1994 | Luhr et al. . |
| 5,425,763 | 6/1995 | Stemmann . |
| 5,538,427 | 7/1996 | Hoffman et al. . |
| 5,540,687 | 7/1996 | Fairley et al. . |
| 5,593,444 | 1/1997 | Svensson et al. . |
| 5,667,507 | 9/1997 | Corin et al. . |
| 5,681,311 | 10/1997 | Foley et al. . |
| 5,690,633 | 11/1997 | Taylor et al. ............................. 606/73 |
| 5,700,263 | 12/1997 | Schendel . |
| 5,725,582 | 3/1998 | Bevan et al. . |
| 5,752,955 | 5/1998 | Errico . |
| 5,769,630 | 6/1998 | Hoffman ........................ 433/7 |

OTHER PUBLICATIONS

Granstrom, et al., "A Detailed Analysis of Titanium Implants Lost in Irradiated Tissues," The International Journal of Oral and Maxillofacial Implants, vol. 9, No. 6, 1994, pp. 653–662.

Eriksson, et al., "Osseointegration from the Perspective of the Plastic Surgeon," Plastic and Reconstructive Surgery, Mar. 1994, pp. 626–637.

Holt, "Osseointegrated Implaints in Oro–Dental and Facial Prosthetic Rehabilitation," Craniofacial Skeletal Augmentation and Replacement, Otolarynogolic Clinics of North America, vol. 27, No. 5, Oct. 1994, pp. 1001–1014.

Tjellstrom, "Osseointegrated for Replacement of Absent or Defective Ears," Clinics in Plastic Surgery, vol. 17, No. 2, Apr. 1990, pp. 355–366.

Product Catalog, Cranio–facial Rehabilitation, Nobelpharma AB, 1991.

"Guidelines for Simulated Surgical Training," Nobelpharma AB, Göteborg, Sweden, date unknown.

Tjellström, et al., "Maxillofacial Reconstruction and Hearing Rehabilitation—Surgeons Manual," University of Göteborg, Göteborg, Sweden, date unknown.

Product Catalog, Branemark System, Nobelpharma AB, 1995.

Holgers, et al., Morphological Evaluation of Clinical Long–Term Percutaneous Titanium Implants, The International Journal of Oral and Maxillofacial Implants, vol. 9, No. 6, 1994, pp. 689–697.

*Primary Examiner*—Hieu Phan
*Attorney, Agent, or Firm*—Ray F. Cox, Jr.

[57] ABSTRACT

A process for non-surgical repositioning of craniofacial bones following surgery for severe disease or trauma. At least two osseointegrated, i.e. bone implanted, fixtures are implanted in the patient. A malleable bar, preferably of a gold, platinum and nickel alloy, is fastened between the two fixtures. The gold bar initially has a flexed shape that could include loops, curves or other nonlinear segments. The flexed gold bar is periodically bent to a more straightened position which thus applies a force between the two bone implanted fixtures. The force between the two fixtures tends to reposition the facial bones over a period of time to restore function and/or form to the injured area.

3 Claims, 4 Drawing Sheets

BONE ANCHORED FIXATION FOR DISPLACEMENT OF FACIAL BONES

BACKGROUND OF THE INVENTION

The present invention relates to the non-surgical repositioning of craniofacial bones following disease or trauma, and in particular, to a process employing osseointegrated fixtures and a malleable bar fixed between the osseointegrated fixtures having at least one non-linear segment which is periodically straightened so as to apply a displacing force between the osseointegrated fixtures.

Craniofacial disease or trauma may often result in the loss of form and/or function to the craniofacial structure. Restoring form and/or function to the craniofacial structure often requires that the craniofacial bones be repositioned to move nearly approximate the natural location of the bones and to allow for the proper fitting of prostheses. Properly formed and fitted prostheses in conjunction with properly positioned craniofacial bones may lead to a succesful restoration of the patient's facial form and lost or impaired function.

The first step is to reposition the craniofacial bones. While surgery is the normal option, it is desirable to avoid, to the extent practicable, major surgical intervention to an area already subjected to severe trauma. Fortunately, bones are capable of migration under steady pressure over a period of time. In fact, the original loss of form or function in some patients may be a result of the migration of bones due to the loss of supporting structure following surgery or trauma.

It is known to use mechanical devices implanted in the bone structure of a patient in order to stabilize the bone structure following surgery. For example, U.S. Pat. No. 5,752,955 to Errico discloses a mechanical cross-link device for use in orthopedic surgery, particularly surgery of the spine, so as to provide increased stability of the spine.

Similarly, U.S. Pat. No. 5,725,582 to Bevan et al. discloses a surgical implant formed from a strand of biocompatible material for the purpose of spinal stabilization.

Furthermore, mechanical devices are known for the displacement of bone structures. U.S. Pat. No. 5,700,263 to Schendel discloses a bone distraction apparatus for osteosynthesis includes a first member housed telescopically within a second member. The two members are attached to bone segments. A ratchet wheel with teeth engages the first member and causes it to telescopically extend from the second member on an arcuate path.

U.S. Pat. No. 5,681,311 issued to Foley, et al. discloses a bone fixation apparatus with plates which slide relative to the other.

Hoffman et al. (U.S. Pat. No. 5,538,427) disclose a palatal wire used in conjunction with a bone anchor.

It is also known to use a periodically bent arch wire in orthodontia to urge teeth to a preferred position. An individual metal band is secured around each tooth. A bracket is then attached to each metal band. The arch wire is then attached to each bracket. In order to effect a realignment of specific teeth, the arch wire must be bent or twisted. The bends or twists in the arch wire are effected while the arch wire is removed from the brackets. After making the requisite bends, the arch wire is reinstalled into the brackets where the bends induce a corrective force on the particular teeth which require repositioning.

The prior art devices are generally mechanically complicated, have difficulty in producing controllable results, and often require major surgical intervention.

The limitations and disadvantages of the prior art are overcome by the present invention as described below.

SUMMARY OF THE INVENTION

The present invention is a process for non-surgical repositioning of craniofacial bones following surgery for severe disease or trauma. At least two osseointegrated fixtures are implanted into the patient and allowed to become integrated into the bone. The position of the fixtures is selected so that the fixtures are osseointegrated into separate bones or bone segments that are relatively movable and where relative movement is desired to reestablish normal facial form and/or function. A bar of malleable material, preferably of a gold, platinum and nickel alloy, is fastened between the two fixtures. A material for the malleable bar is chosen that is amenable to being reshaped and which holds each new shape into which it is formed. The malleable bar initially has a flexed shape that could include loops, curves or other nonlinear segments. The flexed malleable bar is periodically bent to a more straightened position which thus applies a force between the two bone implanted fixtures. The force between the two fixtures tends to reposition the facial bones over a period of time to restore function and/or form to the injured area.

It is therefore an object of the present invention to provide for a process for repositioning craniofacial bones following disease or trauma to restore form and/or function to the craniofacial structure.

It is a further object of the present invention t6 provide for such a process which employs osseointegrated fixtures and a malleable bar fixed therebetween which has an initial flexed shape having at least one non-linear segment.

It is also an object of the present invention to provide for such a process in which the malleable bar is periodically straightened to apply a force between the osseointegrated fixtures to gradually reposition the bones in which the osseointegrated fixtures are implanted.

These and other objects and advantages of the present invention will be apparent from a consideration of the following detailed description of the preferred embodiments in conjunction with the appended drawings as described following.

BRIEF DESCRIPTION OF THE DRAWINGS

FIG. 3 illustrates the preparation of the malleable bars on the mold and the attachment of the malleable bars to the abutments for subsequent assembly onto the osseointegrated implants.

DETAILED DESCRIPTION OF THE PREFERRED EMBODIMENTS

With reference to FIGS. 1A–4, the preferred embodiment of the present invention may be described. The present invention is a process for non-surgical, less invasive repositioning of craniofacial bones following ablative intervention for severe disease or trauma. Following stabilization of craniofacial bone after ablative surgery for neoplastic disease or trauma, facial, head and neck anatomy require repositioning to restore function and/or form to more adequately return the human face, head and jaw to acceptable normal positions. The rigid fixation osseointegration procedure of the present invention provides predictable, safe movement of bone to an acceptable, more functional position for alloplastic restoration and can be used as an adjunct to reconstructive plastic surgery.

Figure 2A:
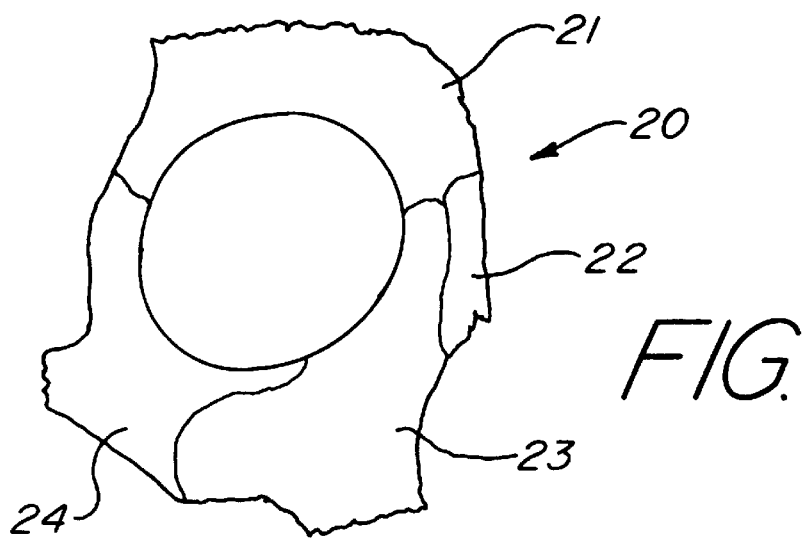
FIG. 2A is a simplified front elevational view of the bone structure of the right orbit.
Figure 2B:
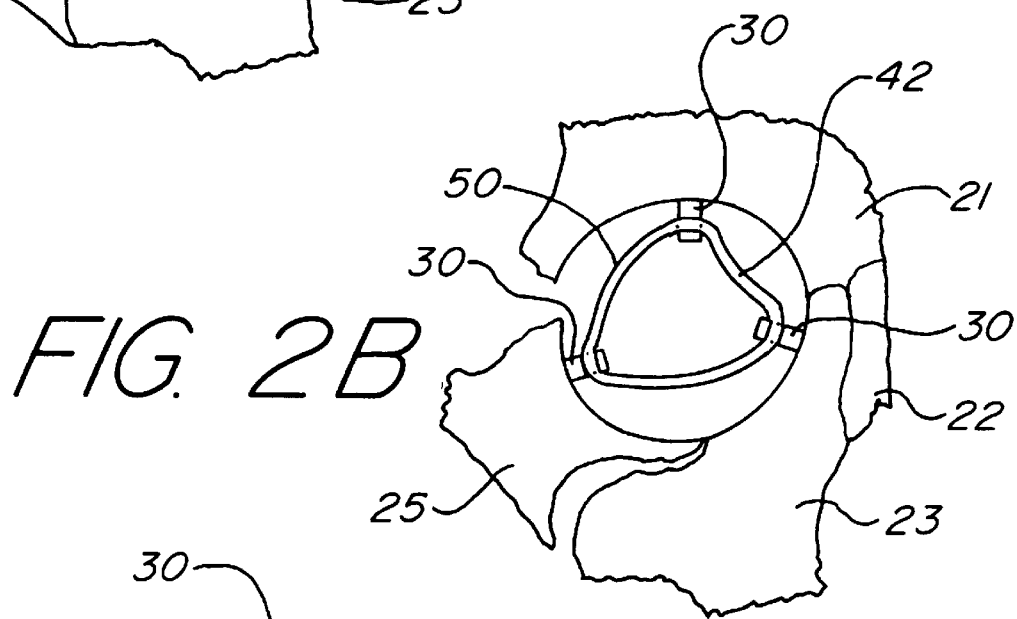
FIG. 2B is a simplified front elevational view of the bone structure of the right orbit in which a portion of the zygomatic bone has been excised and the remaining portion of the zygomatic bone (the "pseudo-zygoma") has moved out of position due to the loss of supporting structure. Osseointegrated fixtures are shown implanted into the bone structure of the right orbit and malleable bars attached therebetween.
Figure 4:
FIG. 4 is a front elevational view of a patient having the malleable bar/abutment assembly attached to previously osseointegrated implants.

FIG. 4 illustrates a patient 10 whose has suffered injury due to trauma or disease to the left orbital area 11. As a result of the injury, the craniofacial bones may require repositioning to restore form and/or function. FIG. 2A illustrates normal facial anatomy of the right orbital area 20. The frontal bone 21, nasal bone 22, maxilla 23 and zygomatic bone 24 are shown. For the purposes of illustration, it is assumed that a portion of the zygomatic bone 24 has been lost due to disease or trauma. The zygomatic bone 24 following the loss of a portion will be referred to hereinafter as the pseudo-zygoma 25. FIG. 2B shows the pseudo-zygoma 25 which has moved out of position with respect to the remainder of the anatomy of the right orbital area 20 due to the loss of supporting structure.

In order to restore the form and/or function to the distorted anatomy of the exemplified right orbital area 20, a plurality of osseointegrated fixtures 30 are implanted into the various bones of the right orbital area 20.

Figure 1A:
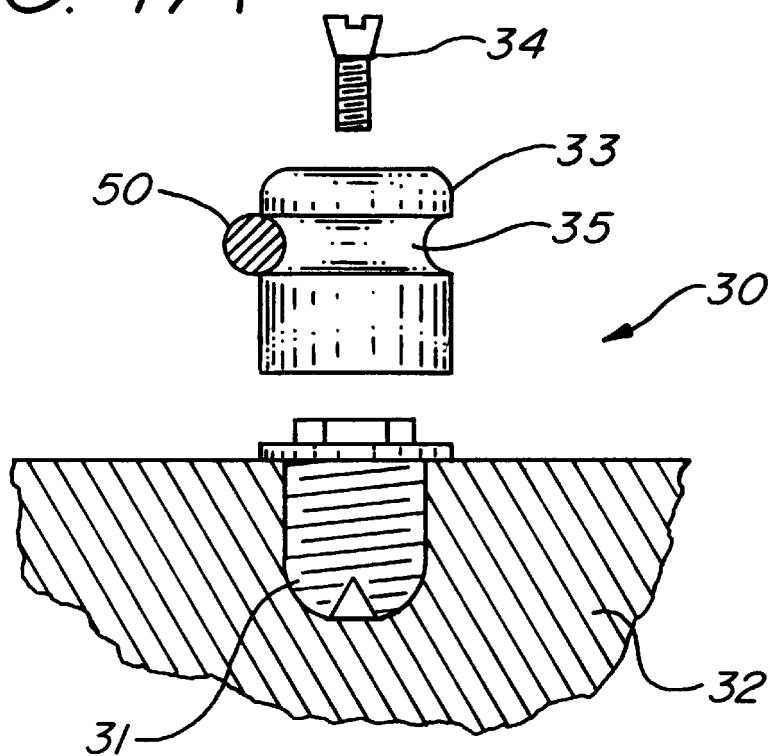
FIG. 1A is an exploded front elevational view of an osseointegrated fixture comprising a percutaneous osseointegrated implant and an abutment external to the skin of the patient. The implant is shown implanted in the bone which is in cross section.

As illustrated in FIG. 1A, each osseointegrated fixture 30 comprises an osseointegrated implant 31 which is implanted into the bone 32 and an abutment 33. The osseointegrated implant 31 is implanted by techniques known in the art and the osseointegrated implant 31 may be any of a number of types known in the art. The implant 31 is allowed to become osseointegrated before proceeding with the process of the present invention.

The abutment 33 is removably affixed to the osseointegrated implant 31 by a screw 34. The abutment 33 is provided with an annular groove 35. The particular form of implant 31 and abutment 33 illustrated in FIG. 1A are known in the art as the Branemark system.

Figure 3:
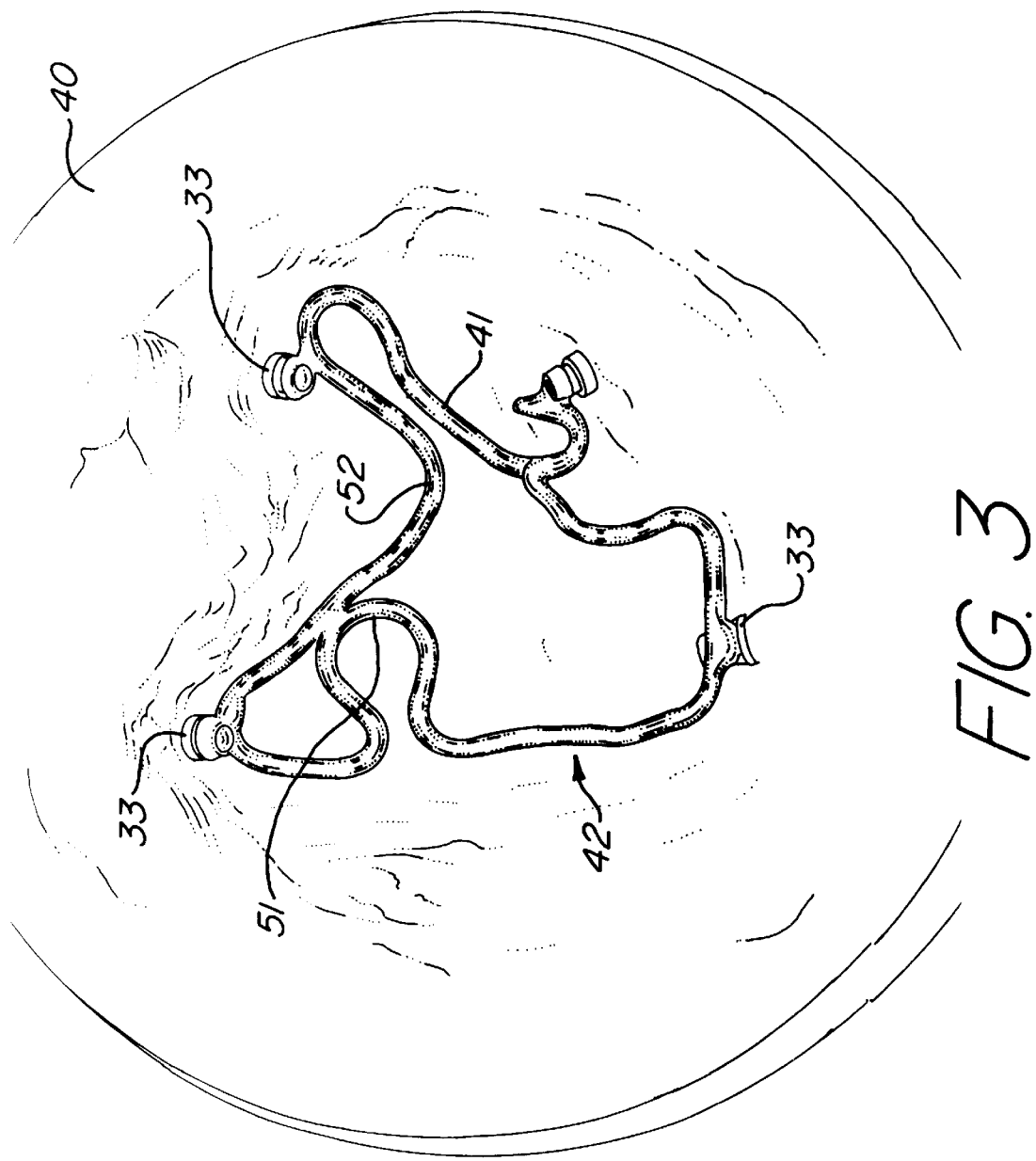
FIG. 3 is a plan view of a mold made from an impression of the anatomy of a patient where osseointegrated implants have been implanted into the bone structure.

After implantation of osseointegrated implants 31 into selected bones such as the frontal bone 21, the maxilla 23 and the pseudozygoma 25, an impression (not shown) is taken of the area using locator pins (not shown) to determine the position of the implants 31 relative to the anatomy of the patient 10. A mold 40 is then formed from the impression, an example of which is shown in FIG. 3. Again using locator pins, abutments 33 may be located on the mold 40 in the correct relative positions to the patient's anatomy. A malleable bar 41 is then welded to the abutments 33 using the annular grooves 35 on the abutments 33 to assist in locating and affixing the malleable bar 41 to the abutments 33. The malleable bar/abutment assembly 42 may then be removed from the mold 40 and attached to the osseointegrated implants 31 on the patient 10 by screws 34 as shown on FIG. 4. Such a technique is known in the art for the purpose of providing a means of attaching a prosthesis. Clips or magnets may be employed for this purpose.

In the practice of the present invention, the malleable bar 41 is made of a material that is capable of being reshaped and which holds each new shape into which it is formed. A alloy of gold, platinum and nickel is desirable. The malleable bar 41 is formed initially with at least one non-linear segment 50 as shown on FIG. 2B. As shown on FIG. 3, the non-linear segment 50 may be in the form of a loop 51, a curve 52, or other non-linear shape which is capable of being straightened.

Figure 1B:
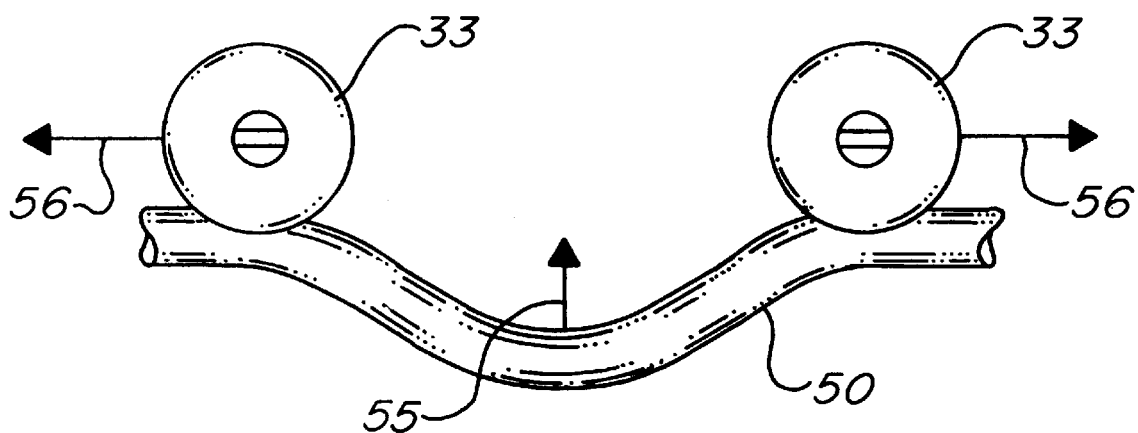
FIG. 1B is a top plan view of a non-linear segment of the malleable bar affixed between two adjacent abutments showing the force applied by straightening the non-linear segment.

After the malleable bar/abutment assembly 42 is affixed to the osseointegrated implants 31, at least one non-linear segment 50 is periodically straightened in the direction shown by the arrow 55 in FIG. 1B so as to apply a force shown by the arrows 56 between adjacent abutments 33.

The force applied between adjacent fixtures 30 tends to reposition the facial bones to which the fixtures 30 are attached. It is desirable to avoid too aggressive a movement of the malleable bar 41 to avoid the formation of connective tissue in the interface between the implant 31 and the bone 32 which could lead to loss of integration.

Figure 2C:
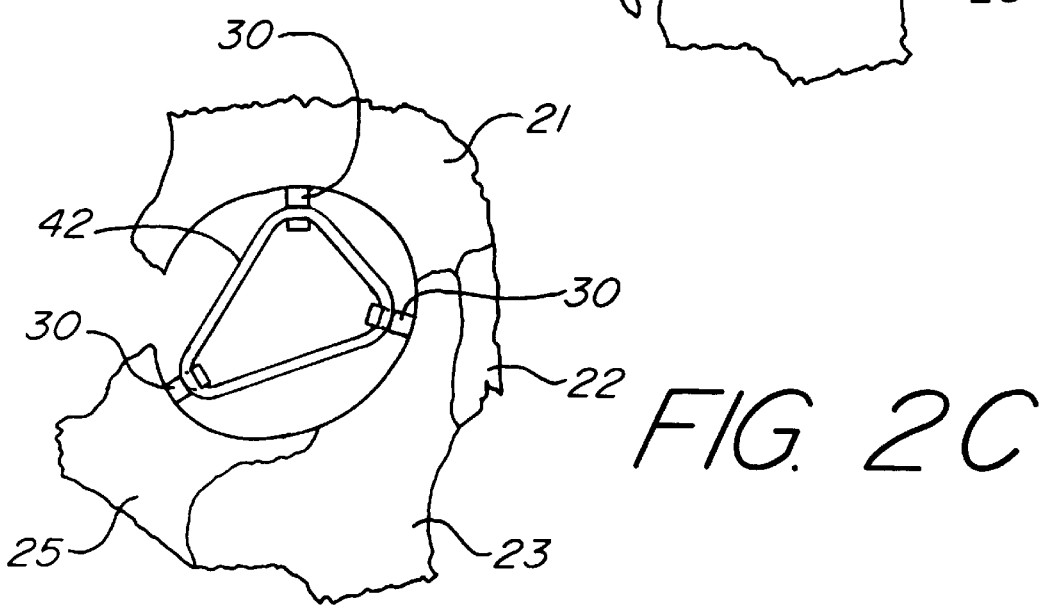
FIG. 2C is a simplified front elevational view of the bone structure of the right orbit showing the movement of the pseudo-zygoma under the influence of the straightened malleable bars.

Over a period of time the patient's craniofacial anatomy may be restored to an approximation of the original or to a form which restores much of the normal functioning lost by the original trauma or disease. Such a restored anatomy is shown in FIG. 2C. In addition to attaining more normal function, the restored form of the craniofacial anatomy allows more realistic and aesthically satisfying restoration of appearance with the addition of better fitting prostheses. Once the desired craniofacial anatomy is restored, the malleable bar may be used as an attachment means for a prosthesis as is known in the art.

A major advantage of the present invention is in predictable results, unlike bone grafting which may result in bone resorption. Done in conjunction with osseointegration, the movement of the bone is to predetermined positions to maximize alloplastic reconstruction, function and appearance. The process may be used for birth defects; i.e., hemi-facial microsomia, and many forms of facial assymetry.

The present invention has been described with reference to certain preferred and alternative embodiments that are intended to be exemplary only and not limiting to the full scope of the present invention as set forth in the appended claims.

What is claimed is:

1. A process for the non-surgical repositioning of the craniofacial bones of a patient following surgery for disease or trauma in order to restore form and/or function to the craniofacial anatomy of the patient, comprising the steps of:

(a) selecting at least two points on the craniofacial bones of the patient between which relative movement to a predetermined position is desirable to restore normal form and/or function to the craniofacial anatomy;

(b) implanting an osseointegrated fixture into each of the selected points on the craniofacial bones of the patient, said osseointegrated fixture comprising a percutaneous osseointegrated implant and an external abutment extending beyond the skin of the patient;

(c) attaching a malleable bar between the abutments of each pair of adjacent osseointegrated fixtures, said malleable bar having at least one non-linear segment;

(d) straightening periodically each of said non-linear segments in situ so as to apply a force between each of said pair of adjacent osseointegrated fixtures until said predetermined position is achieved.

2. The process of claim 1 wherein at least one of said non-linear segments comprises a loop.

3. The process of claim 1 wherein at least one of said non-linear segments comprises a curve.

* * * * *